United States Patent [19]

Turner

[11] Patent Number: 4,962,209

[45] Date of Patent: Oct. 9, 1990

[54] DIHYDROPYRAN DERIVATIVES

[75] Inventor: Ralph W. Turner, Cheadle, England

[73] Assignee: Imperial Chemical Industries PLC, London, England

[21] Appl. No.: 20,960

[22] Filed: Mar. 2, 1987

[30] Foreign Application Priority Data

Mar. 5, 1986 [GB] United Kingdom ................ 8605413

[51] Int. Cl.$^5$ .......................................... C07D 309/30
[52] U.S. Cl. ..................................... 549/419; 549/214
[58] Field of Search ............................... 549/419, 214

[56] References Cited

U.S. PATENT DOCUMENTS

| | | | |
|---|---|---|---|
| 4,269,772 | 5/1981 | Melillo et al. | 540/351 |
| 4,282,148 | 8/1981 | Liu et al. | 540/200 |
| 4,287,123 | 9/1981 | Liu et al. | 540/200 |
| 4,344,885 | 7/1982 | Liu et al. | 549/291 |
| 4,349,687 | 9/1982 | Liu et al. | 549/291 |
| 4,360,684 | 11/1982 | Cvetovich et al. | 549/291 |
| 4,491,659 | 1/1985 | Durette | 536/17.2 |
| 4,559,406 | 12/1985 | Lempert et al. | 549/291 |

FOREIGN PATENT DOCUMENTS 032400 7/1981 European Pat. Off. .
062840 10/1982 European Pat. Off. .

OTHER PUBLICATIONS

Aben et al.; Tetrahedron Letters, vol. 26, No. 15, pp. 1889-1892, 1985; High Pressure-Promoted Cycloadditions of Ketene Acetals and $\alpha\beta$-Unsaturated Aldehydes and Ketones.
Schmidt et al. Tetrahedron Letters, Diasterospecific Synthesis of 2.6-Dideoxy-and 2.4.6-Trideoxy-Sugars via Hetero-Diels-Reaction[1]), vol. 26, p. 2065, 1985.
Danishefsky et al., Tetrahedron Letters, Lanthanide Catalysis of Cycloadditions of Heterodienes with Enol Ethers, vol. 25, p. 721, 1984.
Snider; Tetrahedron Letters, Diels-Alder Reactions of 2-Acetyl-2-Cyclohexenone with Enol Ethers and Emamines, vol. 21, p. 1133, 1980.
Tietze, et al.; Tetrahedron Letters, Hetero-Diels-Alder Reaction of Enaminecarbaldehydes an Entry to Branched Aminosugars, vol. 26, p. 5273, 1985.
Teitze, et al.; Tetrahedron Letters, Diels-Alder Reactions of Malondialdehyde Derivatives with Reversed Electron Demand; An Easy Approach to Structurally Unique Carohydrates and Compounds of the Thromboxane Type, vol. 23, p. 1147, 1982.
Schmidt et al.; Tetrahedron Letters, Hetero-Diels-Alder Reactions of $\alpha$Methoxymethylene Substituted 1.3-Dicarbonyl Compounds with Enol and Enediol Ethers[1]), vol 23, p. 1789, 1982.
Ikota et al.; Chem. Pharm. Bull., Synthetic Studies on Optically Active $\beta$-Lactams.[1]) Stereocontrolled Synthesis of Chiral Thienamycin Intermediate from D--Glucose, vol. 30, p. 1929, 1982.
Hanessian et al.; Can. J. Chem., The Total, Sterocontrolled Synthesis of a Chemical Precursor to (+)-Thienamycin A Formal Synthesis of the Antibiotic[1], vol. 60, p. 2292, 1982.
Wilson et al., The Journal of Antibiotics, vol. xxxvi (9) p. 1109 (1983).
Melillo et al., Tetrahedron Letters, vol. 21, p. 2783 (1980).

Primary Examiner—Nicky Chan
Attorney, Agent, or Firm—Cushman, Darby & Cushman

[57] ABSTRACT

This invention relates to compounds of the formula I

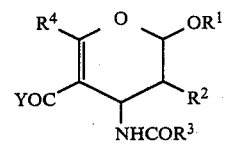

wherein:
R1 is alkyl, cycloalkyl (which alkyl and cycloalkyl groups may be substituted) aryl, arylalkyl or silyl (bearing alkyl, aryl or arylalkyl substituents);
R2 is hydrogen or alkyl;
R3 is hydrogen, alkyl, cycloalkyl (which alkyl and cycloalkyl groups may be substituted), alkenyl, aryl, arylalkyl, amino, mono—or di—alkylamino or a group of the formula —OR5 wherein R5 is optionally substituted alkyl, aryl or arylalkyl;
R4 is alkyl optionally substituted by one or more alkoxy groups or halogen atoms;
Y is optionally substituted alkoxy or cycloalkoxy, arylalkoxy or a group of formula —NR6R7 wherein R6 is hydrogen or alkyl and R7 is .,alkyl, cycloalkyl (which alkyl and cycloalkyl groups may be substituted), aryl or arylalkyl or R7 is a group of formula —COOR8 is alkyl or arylalkyl, which are useful as intermediates in the synthesis of beta-lactam antibiotics, particularly carbapenems, and to a process for the manufacture of the said compounds.

7 Claims, No Drawings

DIHYDROPYRAN DERIVATIVES

This invention relates to compounds useful as intermediates in the synthesis of beta-lactam antibiotics, particularly carbapenems, and to a process for the manufacture of the said compounds.

In this specification chemical formulae (denoted by Roman numerals) are set out graphically on separate sheets. Groups denoted by letter symbols, e.g. R1, R2, Y etc, are to be taken as having the same meaning throughout the specification unless otherwise indicated.

In a first aspect the invention provides compounds of the formula I wherein:

R1 is alkyl, cycloalkyl (which alkyl and cycloalkyl groups may be substituted), aryl, arylalkyl or silyl (bearing alkyl, aryl or arylalkyl substituents);

R2 is hydrogen or alkyl;

R3 is hydrogen, alkyl, cycloalkyl (which alkyl and cycloalkyl groups may be substituted), aryl, arylalkyl or a group of the formula —OR5 wherein R5 is optionally substituted alkyl, aryl or arylalkyl:

R4 is alkyl optionally substituted by one or more alkoxy groups or halogen atoms;

Y is optionally substituted alkoxy or cycloalkoxy, arylalkoxy or a group of formula —NR6R7 wherein R6 is hydrogen or alkyl and R7 is alkyl, cycloalkyl (which alkyl and cycloalkyl groups may be substituted), aryl or arylalkyl or R7 is a group of formula —COOR8 wherein R8 is alkyl or arylalkyl.

In a particular aspect the invention provides compounds of formula I wherein:

R1 is (1-12C)alkyl, cycloalkyl (which alkyl and cycloalkyl groups may be substituted), aryl(1-4C)alkyl or silyl (bearing (1-4C)alkyl, aryl or aryl(1-4C)alkyl substituents):

R2 is hydrogen or (1-4C)alkyl;

R3 is hydrogen, (1-6C)alkyl, cycloalkyl (which alkyl and cycloalkyl groups may be substituted), aryl, aryl(1-4C)alkyl or a group of the formula —OR5 wherein R5 is optionally substituted (1-6C)alkyl, aryl or aryl(1-4C)alkyl:

R4 is (1-6C)alkyl optionally substituted by one or more (1-4C)alkoxy groups or halogen atoms:

Y is (1-6C)alkoxy, cycloalkoxy, aryl(1-4C)alkoxy or a group of formula —NR6R7 wherein R6 is hydrogen or (1-4C)alkyl and R7 is (1-4C)alkyl, cycloalkyl (which alkyl and cycloalkyl groups may be substituted), aryl or aryl(1-4C)alkyl or R7 is a group of formula —COOR8 wherein R8 is (1-4C)alkyl; wherein cycloalkyl means (3-7C)cycloalkyl or bridged (6-9C)bicycloalkyl, cycloalkoxy means (3-7C)cycloalkoxy or bridged (6-9C)bicycloalkoxy and aryl means an optionally substituted 5- or 6-membered carbocyclic or heterocyclic aryl group (containing, when heterocyclic, 1, 2 or 3 heteroatoms selected from O, N and S).

Where any of the above alkyl or cycloalkyl groups are substituted, the substituent(s) may be for example one or more halogen (e.g. fluorine or chlorine) atoms or alkoxy groups unless otherwise specified.

Optional substituent(s) on an alkyl group R5 may be for example one or more halogen (e.g. fluorine or chlorine) atoms.

An optional substituent on an alkoxy or cycloalkoxy group Y may be for example a carboxy or (1-4C)alkoxycarbonyl group.

Optional substituent(s) on an aryl group herein may be for example one or more halogen atoms or (1-6C)alkyl, (1-4C)alkoxy or (2-6C)alkoxycarbonyl groups.

Particular meanings for R1 are methyl, ethyl, benzyl, phenyl, trimethylsilyl and dimethyl-t butylsilyl.

Particular meanings for R2 are hydrogen and methyl.

Particular meanings for R3 are hydrogen, methyl, ethyl, phenyl, benzyl, methoxy, ethoxy, trifluoroethoxy, trichloroethoxy, phenoxy and benzyloxy.

A particular meaning for R4 is methyl optionally substituted by one or more fluorine atoms.

Particular meanings for Y are methoxy, ethoxy, benzyloxy and —NR6R7 wherein R6 is hydrogen and R7 is methyl, ethyl, phenyl, benzyl, α-methylbenzyl, methoxycarbonyl or ethoxycarbonyl.

A particular meaning for an aryl group is phenyl and particular meanings for the optional substituent(s) on an aryl group are fluorine, chlorine, bromine, methyl, ethyl, methoxy, ethoxy, methoxycarbonyl and ethoxycarbonyl.

The compounds of formula I may be prepared for example by reacting a compound of formula II wherein R1 and R2 are as defined above with a compound of formula III wherein R3, R4 and Y are as defined above.

The compounds of formula II and III may each exist in two isomeric forms and the process of the invention extends to the use of either of each pair of isomers separately or of mixtures of isomers.

The reaction is conveniently carried out in an organic solvent eg toluene, xylene, acetonitrile, a halogenated hydrocarbon (e.g. methylene chloride, chloroform), or an ether (e.g. diethyl ether, tetrahydrofuran, dioxan) advantageously in the presence of a catalyst, e.g. a Lewis acid catalyst, in particular a rare earth complex. The use of the catalyst may influence the overall yield of the product and (when $R^2$ is not hydrogen) also the relative amounts of the isomers of products of formula (I) about the C3 and C4 positions which are produced. The reaction is conveniently carried out at temperatures up to about 150° C., e.g. at the boiling point of the solvent.

The compounds of formula I may serve as intermediates for further novel compounds of formula IV which may be prepared for example by oxidation of the compounds of formula I (e.g. by methods analogous to those described in papers of Koga et al, Chem. Pharm. Bull. 30(5) 1929–1931 (1982) and Hanessian et al, Can. J. Chem. 60, 2292(1982)) followed by hydrolysis to form a ketoester of formula V, which may then be reduced, e.g. with sodium borohydride or a hydrosilane or trialkylsilane (e.g. triethylsilane) in acid solution (e.g. in trifluoroacetic acid), conveniently at room temperature, to form the compounds of formula IV. The compounds of formula IV may be converted, by methods known in the literature for analogous compounds or by methods analogous to such methods, (for example D. G. Melillo, I. Shinkai, T. Liu, K. Ryan and M. Sletzinger, Tetrahedron Letters, vol. 21, p. 2783 (1980)) to azetidinones of the formula VI (wherein $R^9$ is, for example, a benzyl group).

Compounds of formula VI are useful intermediates for the production of antibiotics, in particular carbapenem antibiotics.

It will be understood that compounds of formula VI contain up to four asymmetric centres. It is desirable that the said compounds should have the stereochemistry illustrated in formula VIa and the process of the invention is advantageously operated in such a way that compounds having the formula VIa may be produced, e.g. by chiral synthesis, if necessary after subsequent treatment and/or separation of isomers or by resolution of optical isomers at a suitable stage. Achievement of the correct stereochemistry in the compound of formula VIa may be facilitated by the use of compounds of formula I in which one of the groups $R^1$, $R^3$ and Y are chiral.

The invention is illustrated, but not limited, by the following Examples.

EXAMPLE 1

4β-acetylamino-2α-butoxy-5-methoxycarbonyl-6-methyl-3,4-dihydro-2H-pyran

A solution of methyl 2-acetylaminomethylene-3-oxobutanoate (1.0 g) and n-butyl vinyl ether (3.0 ml) in toluene (5 ml) was refluxed for 16 hours. On cooling the reaction mixture a crystalline solid precipitated. Filtration gave the title compound (450 mg) m.p. 154°–156° C. The N.M.R. spectrum in deuterochloroform showed signals with delta values at 0.9 (t,3H): 1.40 (m,2H): 1.60 (m,2H): 1.75 (m,1H): 1.97 (s, 3H); 2.26 (m,1H): 2.28 (s,3H); 3.56 (m,1H): 3.69 (s, 3H): 3.93 (m,1lH); 4.93 (dd, 1H, $J_{2.3e}=2$ Hz, $J_{2.3a}=9$ Hz): 4.9–5.0 148 (m,1H): 5.67 (d, 1H).

EXAMPLE 2

4β-Acetylamino-3α,6-dimethyl-5-methoxycarbonyl-2α-phenoxy-3,4-dihydro-2H-pyran

A mixture of methyl 2-acetylaminomethylene-3-oxobutanoate (1.0 g) and cis-phenyl prop-1-enyl ether (2.0 ml) was stirred at 120° C. for 16 hours. The reaction product was purified by column chromatography on "Merck" silica 9385 using diethyl ether as solvent. Crystallisation from diethyl ether/hexane (1:1) gave the title compound (100 mg), m.p. 108°–109° C. The N.M.R. spectrum in deuterochloroform showed signals with delta values at 1.20 (d,3H): 2.02 (s,3H): 2.24 (m,1H): 2.27 (d,3H); 3.70 (s, 3H): 5.16 (m,1H, $J_{4.3}=9$ Hz): 5.52 (m, 1H, $J_{2.3}<3$ Hz); 5.95 (d,1H): 7.0–7.4 (m,5H).

Chemical Formulae

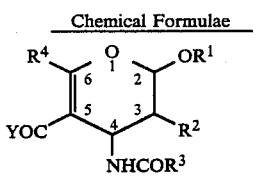
(I)

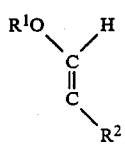
(II)

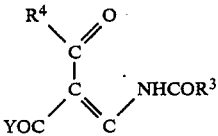
(III)

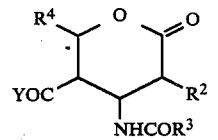
(IV)

-continued
Chemical Formulae

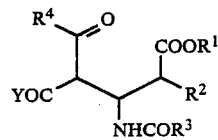
(V)

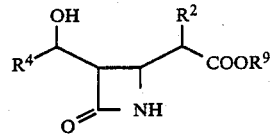
(VI)

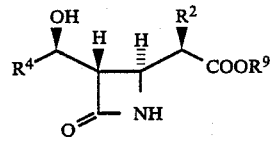
(VIa)

We claim:
1. A dihydropyran derivative of the formula I

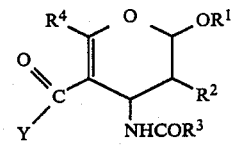
(I)

wherein:
$R^1$ is alkyl, cycloalkyl (which alkyl and cycloalkyl groups may be optionally substituted by one or more halogen atoms or alkoxy groups), phenyl (optionally substituted by one or more of halogen, $C_{1-6}$ alkyl, $C_{1-4}$ alkoxy or $C_{2-6}$ alkoxycarbonyl), phenylalkyl or silyl (bearing alkyl, phenyl or phenylalkyl substituents);
$R^2$ is hydrogen or alkyl;
$R^3$ is hydrogen, alkyl, cycloalkyl (which alkyl and cycloalkyl groups may be optionally substituted by one or more of halogen or alkoxy), phenyl, phenylalkyl or a group of the formula $-OR^5$ wherein $R^5$ is alkyl, alkyl substituted by halogen, phenyl or phenylalkyl;
$R^4$ is alkyl optionally substituted by one or more alkoxy groups or halogen atoms;
Y is alkoxy or cycloalkoxy (which alkoxy and cycloalkoxy groups may be optionally substituted by carboxy or $C_{1-4}$ alkoxycarbonyl), phenylalkoxy or a group of the formula $-NR^6R^7$ wherein $R^6$ is hydrogen or alkyl and
$R^7$ is alkyl, cycloalkyl (which alkyl and cycloalkyl groups may be substituted by one or more halogen atoms or alkoxy groups), phenyl or phenylalkyl or $R^7$ is a group of the formula $-COOR^8$ wherein $R^8$ is alkyl or phenylalkyl.

2. A compound as claimed in claim 1 wherein R1 represents methyl, ethyl, benzyl, phenyl, trimethylsilyl or dimethyl-t-butylsilyl.

3. A compound as claimed in claim 1 wherein R2 represents hydrogen or a methyl group.

4. A compound as claimed in claim 1 wherein R3 represents hydrogen, methyl, ethyl, phenyl, benzyl, methoxy, ethoxy, trifluoroethoxy, trichloroethoxy, phenoxy or benzyloxy.

5. A compound as claimed in claim 1 wherein R4 represents methyl optionally substituted by one or more fluorine atoms.

6. A compound as claimed in claims 1 wherein Y represents methoxy, ethoxy. benzyloxy or —NR6R7 wherein R6 is hydrogen and R7 is methyl, ethyl, phenyl, benzyl, alphamethylbenzyl, methoxycarbonyl or ethoxycarbonyl.

7. A compound as claimed in claim 1 wherein R4 represents methyl.

* * * * *